US011123271B2

(12) United States Patent
Punsch et al.

(10) Patent No.: US 11,123,271 B2
(45) Date of Patent: Sep. 21, 2021

(54) AQUEOUS COSMETIC POWDER COMPOSITION

(71) Applicant: KAO GERMANY GMBH, Darmstadt (DE)

(72) Inventors: Britta Punsch, Darmstadt (DE); Christine Cajan, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 58 days.

(21) Appl. No.: 16/240,236

(22) Filed: Jan. 4, 2019

(65) Prior Publication Data
US 2019/0133902 A1 May 9, 2019

Related U.S. Application Data

(62) Division of application No. 15/308,558, filed as application No. PCT/EP2015/059836 on May 5, 2015, now abandoned.

(30) Foreign Application Priority Data

May 7, 2014 (EP) .................................... 14167356

(51) Int. Cl.
*A61K 8/25* (2006.01)
*A61K 8/60* (2006.01)
*A61K 8/22* (2006.01)
*A61K 8/02* (2006.01)
*A61K 8/34* (2006.01)
*A61K 8/37* (2006.01)
*A61K 8/41* (2006.01)
*A61K 8/46* (2006.01)
*A61K 8/49* (2006.01)
*A61K 8/81* (2006.01)
*A61K 8/891* (2006.01)
*A61Q 5/06* (2006.01)

(52) U.S. Cl.
CPC ............... *A61K 8/25* (2013.01); *A61K 8/022* (2013.01); *A61K 8/0241* (2013.01); *A61K 8/22* (2013.01); *A61K 8/345* (2013.01); *A61K 8/37* (2013.01); *A61K 8/411* (2013.01); *A61K 8/466* (2013.01); *A61K 8/4946* (2013.01); *A61K 8/60* (2013.01); *A61K 8/602* (2013.01); *A61K 8/8158* (2013.01); *A61K 8/8176* (2013.01); *A61K 8/8182* (2013.01); *A61K 8/891* (2013.01); *A61Q 5/06* (2013.01); *A61Q 5/065* (2013.01); *A61K 2800/432* (2013.01); *A61K 2800/4322* (2013.01); *A61K 2800/524* (2013.01); *A61K 2800/54* (2013.01); *A61K 2800/5424* (2013.01); *A61K 2800/5426* (2013.01); *A61K 2800/5428* (2013.01); *A61K 2800/805* (2013.01); *A61K 2800/88* (2013.01)

(58) Field of Classification Search
CPC .......... A61K 8/25; A61K 8/022; A61K 8/345; A61K 8/8182; A61K 8/0241; A61K 8/466; A61K 8/891; A61K 2800/54; A61K 8/8135; A61K 2800/31; A61K 2800/413; A61K 2800/432; A61K 2800/4322; A61K 2800/48; A61K 2800/524; A61K 2800/5424; A61K 2800/5426; A61K 2800/5428; A61K 2800/59; A61K 2800/61; A61K 2800/622; A61K 2800/651; A61K 2800/652; A61K 2800/805; A61K 2800/88; A61K 8/22; A61K 8/355; A61K 8/37; A61K 8/411; A61K 8/42; A61K 8/442; A61K 8/4946; A61K 8/585; A61K 8/60; A61K 8/602; A61K 8/8158; A61K 8/8176; A61K 8/88; A61K 8/90; A61Q 5/06; A61Q 5/065; A61Q 1/12; A61Q 5/10; A61Q 19/00; A61Q 5/02

See application file for complete search history.

(56) References Cited

U.S. PATENT DOCUMENTS

| 8,021,651 | B2 | 9/2011 | Hentrich et al. |
| 2004/0180069 | A1 | 9/2004 | Bleuez |
| 2008/0233071 | A1 | 9/2008 | Hentrich et al. |
| 2009/0217465 | A1* | 9/2009 | Cremer ..................... A61K 8/25 8/405 |
| 2009/0304757 | A1* | 12/2009 | Herve ...................... A61Q 5/02 424/401 |
| 2014/0302106 | A1 | 10/2014 | Knappe et al. |
| 2015/0132244 | A1 | 5/2015 | Knappe et al. |
| 2017/0049670 | A1 | 2/2017 | Punsch et al. |

FOREIGN PATENT DOCUMENTS

| DE | 1457191 A2 * | 9/2004 | ............... A61K 7/02 |
| DE | 102005052585 A1 | 5/2007 | |
| DE | WO2007051511 A1 * | 6/2007 | ............... A51Q 5/06 |
| DE | 102011088840 A1 | 6/2013 | |
| DE | 102012211912 A1 | 1/2014 | |

(Continued)

OTHER PUBLICATIONS

EP1457191A2, Bluez, Lois, et al. translation (Year: 2004).*

(Continued)

Primary Examiner — Audrea B Coniglio
(74) Attorney, Agent, or Firm — Norris McLaughlin, P.A.

(57) ABSTRACT

The present invention relates to an aqueous cosmetic powder composition especially designed for styling hair comprising water, hydrophobic colloidal silica and a water soluble non-ionic polyol having at least three hydroxyl groups and is solid at ambient temperature.

16 Claims, No Drawings

(56) References Cited

FOREIGN PATENT DOCUMENTS

| EP | 1 457 191 A | 9/2004 |
|----|-------------|--------|
| WO | 2005/034917 A2 | 4/2005 |
| WO | 2007/051511 A | 5/2007 |
| WO | 2010/054980 A | 5/2010 |

OTHER PUBLICATIONS

WO2007051511A1, Hentrich, Dirk, et al., translation (Year: 2006).*
International Search Report for corresponding application PCT/EP2015/059836 dated Aug. 24, 2015.
Written Opinion of the International Searching Authority for corresponding application PCT/EP2015/059836 dated Aug. 24, 2015.
"Hydrophobe pyrogene Kieselsaure", AEROSIL® R 202, "Degussa", Mar. 4, pp. 1-14.

* cited by examiner

AQUEOUS COSMETIC POWDER COMPOSITION

This application is a divisional of U.S. application Ser. No. 15/308,558, filed Nov. 2, 2016, which is a § 371 U.S. National stage of PCT International Patent Application No. PCT/EP2015/059836, filed May 5, 2015, which claims foreign priority benefit under 35 U.S.C. § 119 of European Application No. 14167356.6, filed May 7, 2014, the disclosures of each of which patent applications are incorporated herein by reference.

The present invention relates to an aqueous cosmetic powder composition especially designed for styling hair comprising water, hydrophobic silica and a water soluble non-ionic polyol having at least three hydroxyl groups and is solid at 25° C.

Aqueous powdered hair cosmetic compositions applied onto hair for styling have been known for some time. They have excellent hair styling and setting effects, however they are difficult to remove from hair simply by shampooing hair because of hydrophobic nature of the powder which affects considerably the touch feel of the hair and the performances of the subsequently used products and aggravates in cases where the chemical reaction has to take place in order to alter and/or give hair improved cosmetic properties.

WO 01/37800 discloses powdered aqueous compositions for skin conditioning which may comprise highly water soluble polymers. DE 10 2008 057 261 A1 discloses powdered aqueous compositions comprising film forming and/or setting polymers in the aqueous phase. None of these documents disclose a composition comprising a polyol as required in the compositions of present invention. It has been observed that removability of these powder compositions from hair is not easy and mostly they may not be removed from hair with washing hair with a conventional shampoo composition.

The aim of the present invention has been to provide aqueous cosmetic powder composition for hair which provides effective hair styling and setting but at the same time may easily be removed from hair by simple subsequent washing hair with a conventional shampoo composition.

After a long search, the present inventors have found out that powder cosmetic composition comprising hydrophobic colloidal silica, water and a water soluble non-ionic polyol having at least three hydroxyl groups and is solid at ambient temperature has good setting and styling effects on the hair and may also be washed out easily by a conventional shampoo composition.

Accordingly the first object of the present invention is an aqueous cosmetic powder composition comprising water, hydrophobic colloidal silica and a water soluble non-ionic polyol having at least three hydroxyl groups and solid at ambient temperature, 25° C.

The second object of the present invention is the use of the composition for setting and/or styling hair.

The third object is the process for styling and/or setting hair wherein the composition of the present invention is applied onto dry hair.

The fourth object is a kit for hair comprising the composition of the present invention.

The fifth object is a process for producing the composition of the present invention wherein the water soluble polyol with at least three hydroxyl groups and solid at 25° C. is dissolved in water and hydrophobic colloidal silica is added to the composition and the mixture is mixed at high shear rate at ambient temperature.

In the above mentioned process, in case other powder ingredients are present they are simply added to the composition after producing the powder aqueous composition.

The powder composition of the present invention comprises water less than 80% by weight, preferably in the range of 25 to 75% by weight, more preferably 30 to 65% by weight and most preferably 40 to 60% by weight, all values are calculated to the total composition.

Hydrophobic colloidal silica is comprised in the compositions at a concentration up to 25% by weight, preferably 1 to 20% by weight, more preferably 2 to 15% and most preferably 3 to 15% by weight, all values are calculated to the total composition. The hydrophobic colloidal silica suitable for the purpose of the present invention has the BET surface area in the range of 190 and 250 m2/g and has a tamped density in the range of 55 to 65 g/l according to DIN EN ISO 787/11, August 1983.

The compositions of the present invention comprise a water soluble non-ionic polyol having at least three hydroxyl groups and solid at ambient temperature. In an embodiment, the polyol comprises at least 5 hydroxyl groups. The suitable polyols are sorbitol, saccharose, glucose, lactose, fructose and other polyols solid at ambient temperature. The most preferred polyol is sorbitol.

Concentration of one or more polyol(s) is up to 45% by weight, preferably in the range of 5 to 40%, more preferably 10 to 35% and most preferably 15 to 35% by weight, all values are calculated to the total composition.

The compositions may also comprise one or more film forming and/or setting polymers. Suitable ones are those known anionic, non-ionic, cationic and amphoteric polymers. Concentration of one or more such polymers may be in the range of 0.1 to 10% by weight, preferably in the range of 0.5 to 7.5% by weight, more preferably 1 to 5% and most preferably 1 to 3.5% by weight, all values are calculated to the total composition.

Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64, Plus from BASF AG.

As amphoteric polymers which can be used alone or in mixture with at least one additional nonionic polymer, reference is here made in particular to copolymers of N-octyl acrylamide, (meth)acrylic acid and tert.-butyl aminoethyl methacrylate of the type "Amphomer®", copolymers from methacryloyl ethyl betaine and alkyl methacrylates of the type "Yukaformer®", e.g. the butyl methacrylate copolymer "Yukaformer® Am75"; copolymers from monomers containing carboxyl groups and sulfonic groups, e.g. (meth) acrylic acid and itaconic acid, with monomers such as mono- or dialkyl aminoalkyl (meth)acrylates or mono- or dialkyl aminoalkyl (meth)-acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199.

Suitable anionic polymers alone or in combination with non-ionic polymers are vinyl-alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof.

Further suitable anionic polymers are Acrylate copolymers available under trade name Salcare SC 81, PEG/PPG 25/25 dimethicone/acrylate copolymer available under trade name Luviflex Silk from BASF, Acrylates/t-butylacrylamide copolymer available under trade name Ultrahold Strong, Advantage LC-E which is vinylcaprolactam/PVP/dimethylaminoethylmethacrylate copolymer and VA/crotonates copolymer available under trade name Luviset CA 66.

Suitable cationic polymers are such as Polyquaternium 11, Polyquaternium 16, Polyquaternium 22 and Polyquaternium 28, Polyquaternium 30, Polyquaternium 37, Polyquaternium 36, Polyquaternium 46, Polyquaternium 24, Polyquaternium 67, and Polyquaternium 72.

The compositions of the present invention may also be used for colour giving to hair. In such a case, the compositions may also comprise one or more hair direct dyes, preferably selected from non-ionic nitro dyes, anionic dyes and cationic dyes.

Non-limiting examples to cationic dyes are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Further suitable direct dyes are anionic dye. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of direct dyes in the compositions of the present invention is within the range of 0.001 to 5%, preferably 0.01 to 3% and more preferably 0.05 to 2%, and most preferably 0.1 to 1% by weight calculated to total composition, calculated to total composition.

The aqueous core of the powder composition may additionally comprise preservatives such as parabens such as methyl, ethyl and propyl parabens, hydantoins such as DMDM hydantoin, aromatic carboxylic acids such as benzoic acid and/or its salts. Concentration of such preservatives is certainly dependent upon the type used but typically may vary within 0.01 and 1% by weight, calculated to the total composition.

Compositions of the present invention may contain UV filters either for stabilization of the product colour and/or for protection of hair from environmental influences such as loss of elasticity, loss of hair colour (bleaching effect of sun light). Suitable UV-absorbing substance are Polysilicone-15, 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher.

The suitable amount of the UV-absorber ranges from about 0.01% to 1% by weight, calculated to the total composition. Attention should be paid to the stability and solubility especially when using UV filter as salts, e.g. anionic UV filter salts.

The compositions according to the invention may also comprise further agents, such as proteins, for example bamboo protein, and protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®", "Herbasol®", "Sedaplant®" and "Hexaplant®". Extracts and the preparation thereof are also described in "Hagers Handbuch der pharmazeutischen Praxis". $4^{th}$ Ed.

The composition may also comprise one or more oil. The attention should be paid that the powder properties of the composition must not be lost when oil is added to the composition. This may also relate to the concentration of the oil added.

Suitable oils are fragrance oils, silicones such as volatile or non-volatile, natural and synthetic oils. Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule such as trimethyl pentaphenyl trisiloxane, natural oils such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

The concentration of oil is in the range of 0.001 to 2%, preferably 0.005 to 1.5% and most preferably 0.01 to 1% by weight calculated to the total of the composition.

The following examples are to illustrate the invention but not to limit it.

The compositions were prepared by dissolving the polyol in water and combining it with hydrophobic colloidal silica and homogenizing it at high shear rate. The powder polymers were subsequently combined with the powder composition.

EXAMPLE 5

|  | % by weight |
| --- | --- |
| Part A | |
| Water | q.s. to 100 |
| Saccharose | 21.0 |
| DMDM-Hydantoin | 0.3 |
| Part B | |
| Hydrophobic colloidal silica | 10.0 |
| Part C | |
| Fragrance | 0.30 |
| Part D | |
| Acrylates/octylacrylamide copolymer | 2.0 |

The composition was produced by combining Parts A and B and mixing in a high shear mixer and subsequently the Parts C and D were added while mixing.

The composition was applied onto clean dry hair and provides improved setting and styling benefits. Additionally it was easily washed out with a conventional shampoo composition.

EXAMPLE 6

|  | % by weight |
| --- | --- |
| Part A | |
| Water | q.s. to 100 |
| Sorbitol | 21.0 |
| DMDM-Hydantoin | 0.3 |

TABLE I

| | Example 1 | Comp. 1 | Comp. 2 | Comp. 3 | Example 2 | Example 3 | Example 4 |
| --- | --- | --- | --- | --- | --- | --- | --- |
| Hydrophobic colloidal silica Aerosil R 812S | 5.00 | 5.00 | 5.00 | 5.00 | 5.00 | 5.00 | 5.00 |
| Water | to 100 | to 100 | to 100 | to 100 | to 100 | to 100 | to 100 |
| PVP Luviskol K90 (Powder) | — | — | 2.00 w % | — | — | — | — |
| Octylacrylamide/ Acrylater/ Butylaminoethyl Methacrylate Copolymer Amphomer 28-4910 | — | — | — | 2.00 w % | — | — | — |
| Sorbitol | 21.00 | — | — | — | — | — | — |
| Saccharose | — | — | — | — | 21.00 | — | — |
| Fruktose | — | — | — | — | — | 21.00 | — |
| Glucose | — | — | — | — | — | — | 21.00 |
| DMDM-Hydantoin | 0.30 | 0.30 | 0.30 w % | 0.30 w % | 0.30 | 0.30 | 0.30 |
| Styling-Effect 1 Bad 5 Very good | 5 | 3 | 4 | 5 | 5 | 5 | 5 |
| Wet with Water | YES | NO | NO | NO | YES | YES | YES |
| Washed out after one shampoo | YES | NO | NO | NO | YES | YES | YES |

-continued

|  | % by weight |
| --- | --- |
| Part B |  |
| Hydrophobic colloidal silica | 10.0 |
| Part C |  |
| Fragrance | 0.30 |
| Part D |  |
| PVP powder | 2.0 |

The composition was produced by combining Parts A and B and mixing in a high shear mixer and subsequently the Parts C and D were added while mixing.

The composition was applied onto clean dry hair and provides improved setting and styling benefits. Additionally it was easily washed out with a conventional shampoo composition.

EXAMPLE 7

|  | % by weight |
| --- | --- |
| Part A |  |
| Water | q.s. to 100 |
| Sorbitol | 21.0 |
| DMDM-Hydantoin | 0.3 |
| Polyquaternium-11 | 0.2 |
| Part B |  |
| Hydrophobic colloidal silica | 15.0 |
| Part C |  |
| Fragrance | 0.30 |

The composition was produced by combining Parts A and B and mixing in a high shear mixer and subsequently the Part C was added while mixing.

The composition was applied onto clean dry hair and provides improved setting and styling benefits. Additionally it was easily washed out with a conventional shampoo composition.

EXAMPLE 8

|  | % by weight |
| --- | --- |
| Part A |  |
| Water | q.s. to 100 |
| Sorbitol | 21.0 |
| Basic Violet 2 | 0.05 |
| DMDM-Hydantoin | 0.3 |
| Part B |  |
| Hydrophobic colloidal silica | 5.0 |
| Part C |  |
| Fragrance | 0.30 |

The composition was produced by combining Parts A and B and mixing in a high shear mixer and subsequently the Part C was added while mixing.

The composition was applied onto clean dry hair and provides improved setting and styling benefits in addition to a light colour shine effect. Additionally it was easily washed out with a conventional shampoo composition.

EXAMPLE 9

|  | % by weight |
| --- | --- |
| Part A |  |
| Water | q.s. to 100 |
| Sorbitol | 21.0 |
| Basic Violet 2 | 0.05 |
| DMDM-Hydantoin | 0.3 |
| Part B |  |
| Hydrophobic colloidal silica | 7.0 |
| Part C |  |
| Fragrance | 0.30 |

The composition was produced by combining Parts A and B and mixing in a high shear mixer and subsequently the Part C was added while mixing.

The composition was applied onto clean dry hair and provides improved setting and styling benefits in addition to a light colour shine effect. Additionally it was easily washed out with a conventional shampoo composition.

EXAMPLE 10

|  | % by weight |
| --- | --- |
| Part A |  |
| Water | q.s. to 100 |
| Sorbitol | 21.0 |
| HC Blue No 9 | 0.05 |
| DMDM-Hydantoin | 0.3 |
| Part B |  |
| Hydrophobic colloidal silica | 12.0 |
| Part C |  |
| Fragrance | 0.30 |

The composition was produced by combining Parts A and B and mixing in a high shear mixer and subsequently the Part C was added while mixing.

The composition was applied onto clean dry hair and provides improved setting and styling benefits in addition to a light blue colour shine effect. Additionally it was easily washed out with a conventional shampoo composition.

EXAMPLE 11

|  | % by weight |
| --- | --- |
| Part A |  |
| Water | q.s. to 100 |
| Sorbitol | 21.0 |
| Acid Blue 1 | 0.05 |
| DMDM-Hydantoin | 0.3 |
| Part B |  |
| Hydrophobic colloidal silica | 10.0 |
| Part C |  |
| Fragrance | 0.30 |

The composition was produced by combining Parts A and B and mixing in a high shear mixer and subsequently the Part C was added while mixing.

The composition was applied onto clean dry hair and provides improved setting and styling benefits in addition to a light blue colour shine effect. Additionally it was easily washed out with a conventional shampoo composition.

EXAMPLE 12

|  | % by weight |
| --- | --- |
| Part A | |
| Water | q.s. to 100 |
| Fructose | 10.0 |
| HC Blue No 5 | 0.05 |
| Acid Blue 1 | 0.05 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |

The composition was produced by combining Parts A and B and mixing in a high shear mixer and subsequently the Part C was added while mixing.

The composition was applied onto clean dry hair and provides improved setting and styling benefits in addition to a blue colour shine effect. Additionally it was easily washed out with a conventional shampoo composition.

EXAMPLE 13

|  | % by weight |
| --- | --- |
| Part A | |
| Water | q.s. to 100 |
| Panthenol | 0.10 |
| Sorbitol | 25.0 |
| HC Blue No 9 | 0.05 |
| Basic red 51 | 0.05 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |

The composition was produced by combining Parts A and B and mixing in a high shear mixer and subsequently the Part C was added while mixing.

The composition was applied onto clean dry hair and provides improved setting and styling benefits in addition to a light blue colour shine effect. The composition provides effective protection against UV light. Additionally it was easily washed out with a conventional shampoo composition.

EXAMPLE 14

|  | % by weight |
| --- | --- |
| Part A | |
| Water | q.s. to 100 |
| Sorbitol | 25.0 |
| HC Blue No 9 | 0.05 |
| Acid blue 1 | 0.05 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |
| Part D | |
| Oryza sativa (Rice) starch | 0.5 |

The composition was produced by combining Parts A and B and mixing in a high shear mixer and subsequently the Parts C and D were added while mixing.

The composition was applied onto clean dry hair and provides improved setting and styling benefits in addition to a light blue colour shine effect. The composition provides effective protection against UV light. Additionally it was easily washed out with a conventional shampoo composition.

EXAMPLE 15

|  | % by weight |
| --- | --- |
| Part A | |
| Water | q.s. to 100 |
| Sorbitol | 25.0 |
| HC Blue No 9 | 0.05 |
| Acid blue 1 | 0.05 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |
| Part D | |
| Calcium sulphate | 0.5 |

The composition was produced by combining Parts A and B and mixing in a high shear mixer and subsequently the Parts C and D were added while mixing.

The composition was applied onto clean dry hair and provides improved setting and styling benefits in addition to a light blue colour shine effect. The composition provides effective protection against UV light. Additionally it was easily washed out with a conventional shampoo composition.

EXAMPLE 16

| | % by weight |
|---|---|
| Part A | |
| Water | q.s. to 100 |
| Sorbitol | 25.0 |
| *Bambusa vulgaris* shoot extract | 0.1 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |

The composition was produced by combining Parts A and B and mixing in a high shear mixer and subsequently the Parts C and D were added while mixing.

The composition was applied onto clean dry hair and provides improved setting and styling benefits. The composition provides effective protection against UV light. Additionally it was easily washed out with a conventional shampoo composition.

EXAMPLE 17

| | % by weight |
|---|---|
| Part A | |
| Water | q.s. to 100 |
| Sorbitol | 25.0 |
| Lactic acid | 0.005 |
| Malic acid | 0.005 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |
| Dimethicone 5 cSt | 0.50 |

The composition was produced by combining Parts A and B and mixing in a high shear mixer and subsequently the Part C was added while mixing.

The composition was applied onto clean dry hair and provides improved setting and styling benefits. The composition provides effective protection against UV light. Additionally it was easily washed out with a conventional shampoo composition.

EXAMPLE 18

| | % by weight |
|---|---|
| Part A | |
| Water | q.s. to 100 |
| Sorbitol | 25.0 |
| Lactic acid | 0.005 |
| Malic acid | 0.005 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |
| Castor oil | 0.50 |

The composition was produced by combining Parts A and B and mixing in a high shear mixer and subsequently the Part C was added while mixing.

The composition was applied onto clean dry hair and provides improved setting and styling benefits. The composition provides effective protection against UV light. Additionally it was easily washed out with a conventional shampoo composition.

EXAMPLE 19

| | % by weight |
|---|---|
| Part A | |
| Water | q.s. to 100 |
| Sorbitol | 25.0 |
| Lactic acid | 0.005 |
| Malic acid | 0.005 |
| DMDM-Hydantoin | 0.3 |
| Part B | |
| Hydrophobic colloidal silica | 10.0 |
| Part C | |
| Fragrance | 0.30 |
| Ethylhexyl methoxycinnamate | 0.20 |
| Paraffin oil | 0.50 |

The composition was produced by combining Parts A and B and mixing in a high shear mixer and subsequently the Part C was added while mixing.

The composition was applied onto clean dry hair and provides improved setting and styling benefits. The composition provides effective protection against UV light. Additionally it was easily washed out with a conventional shampoo composition.

The invention claimed is:

1. A process for styling and/or setting hair comprising:
applying an aqueous powder cosmetic composition onto dry hair, wherein the aqueous powder cosmetic composition comprises:
water;
hydrophobic colloidal silica;
a water-soluble non-ionic polyol having at least five hydroxyl groups, being solid at 25° C., and being present in the aqueous powder cosmetic composition in an amount of at least 21 wt % and up to 45 wt %, calculated to the total of the aqueous powder cosmetic composition;
one or more film forming and/or setting polymer; and
at least one of setting and styling the hair with the aqueous powder cosmetic composition applied thereon.

2. A process for producing an aqueous powder cosmetic composition which comprises water, hydrophobic colloidal silica, a water-soluble non-ionic polyol having at least five hydroxyl groups and being solid at 25° C., and one or more film forming and/or setting polymer, the process comprising:

dissolving the polyol in water to produce a mixture A;

adding the hydrophobic colloidal silica to the mixture A to produce a mixture B;

homogenizing the mixture B at high shear rate at ambient temperature to produce the aqueous powder cosmetic composition; and combining the one or more film forming and/or setting polymer with the aqueous powder cosmetic composition, wherein the polyol is present in the aqueous powder cosmetic composition in an amount of at least 21 wt % and up to 45 wt %, calculated to the total of the aqueous powder cosmetic composition.

3. A kit for hair comprising an aqueous powder cosmetic composition, wherein the aqueous powder cosmetic composition comprises:

water;

hydrophobic colloidal silica;

at least one preservative selected from at least one paraben, at least one hydantoin, at least one aromatic carboxylic acid, and its salt, wherein the at least one preservative is present at a concentration range within 0.01% and 1% by weight, calculated to a total of the aqueous powder cosmetic composition;

a water-soluble non-ionic polyol having at least five hydroxyl groups, being solid at 25° C., and present in the aqueous powder cosmetic composition in an amount of at least 21 wt % and up to 45 wt %, calculated to the total of the aqueous powder cosmetic composition; and one or more film forming and/or setting polymer.

4. The process according to claim 1, wherein the aqueous powder cosmetic composition comprises less than 80% by weight of water, calculated to the total of the aqueous powder cosmetic composition.

5. The process according to claim 1, wherein the aqueous powder cosmetic composition comprises up to 15% by weight of hydrophobic silica, calculated to the total of the aqueous powder cosmetic composition.

6. The process according to claim 1, wherein the hydrophobic silica has a BET specific surface area in the range of 190 to 250 m$^2$/g, and tamped density in the range of 55 to 65 g/L, according to DIN EN ISO 787/11 of August 2013.

7. The process according to claim 1, wherein the polyol has at least five hydroxyl groups.

8. The process according to claim 1, wherein the polyol is selected from sorbitol, saccharose, glucose, lactose, and fructose.

9. The process according to claim 1, wherein the polyol is sorbitol.

10. The process according to claim 1, wherein the one or more film forming and/or setting polymer is selected from the group consisting of anionic polymers, non-ionic polymers, cationic polymers, and amphoteric polymers and present at a concentration range of 0.1 to 10% by weight, calculated to a total of the aqueous powder cosmetic composition.

11. The process according to claim 1, wherein the aqueous powder cosmetic composition comprises one or more hair direct dyes.

12. The process according to claim 1, wherein the aqueous powder cosmetic composition comprises one or more UV filter.

13. The process of claim 1, wherein the hydrophobic colloidal silica is present in the aqueous powder cosmetic composition in an amount of 7 wt % or greater, calculated to a total of the aqueous powder cosmetic composition.

14. The process of claim 13, wherein the hydrophobic colloidal silica is present in the aqueous powder cosmetic composition in an amount of 10 wt % or greater, calculated to a total of the aqueous powder cosmetic composition.

15. The process of claim 1, the aqueous powder cosmetic composition further comprises at least one preservative selected from at least one paraben, at least one hydantoin, at least one aromatic carboxylic acid, and its salt, wherein the at least one preservative is present at a concentration range within 0.01% and 1% by weight, calculated to a total of the aqueous powder cosmetic composition.

16. The process of claim 2, wherein the mixture A further comprises at least one preservative selected from at least one paraben, at least one hydantoin, at least one aromatic carboxylic acid, and its salt, wherein the at least one preservative is present at a concentration range within 0.01% and 1% by weight, calculated to a total of the aqueous powder cosmetic composition.

* * * * *